United States Patent
Martinez Lopez

(10) Patent No.: US 10,073,046 B2
(45) Date of Patent: Sep. 11, 2018

(54) DEVICE FOR EXAMINING WAFERS AND WAFER CONNECTIONS IN THE BASE OF THE HOUSINGS OF LIGHT-EMITTING DIODES THROUGH THE TRANSPARENT DOMES THEREOF

(71) Applicant: QUIMICA TECH, S.A. DE C.V., Chihuahua (MX)

(72) Inventor: Jose Manuel Martinez Lopez, Chihuahua (MX)

(73) Assignee: QUIMICA TECH, S.A. De C.V., Chihuahua (MX)

( * ) Notice: Subject to any disclaimer, the term of this patent is extended or adjusted under 35 U.S.C. 154(b) by 0 days.

(21) Appl. No.: 15/559,476

(22) PCT Filed: Mar. 22, 2016

(86) PCT No.: PCT/MX2016/000030
§ 371 (c)(1),
(2) Date: Sep. 19, 2017

(87) PCT Pub. No.: WO2016/163869
PCT Pub. Date: Oct. 13, 2016

(65) Prior Publication Data
US 2018/0113080 A1  Apr. 26, 2018

(30) Foreign Application Priority Data
Apr. 10, 2015 (MX) ............... MX/a/2015/004603

(51) Int. Cl.
*G01N 21/00* (2006.01)
*G01J 5/02* (2006.01)
*G01N 21/95* (2006.01)

(52) U.S. Cl.
CPC .................. *G01N 21/9501* (2013.01)

(58) Field of Classification Search
CPC ........... G01N 21/9501; G01N 21/8806; G01N 21/00; G01N 21/94; G01N 21/956; G01N 2223/6116; G01N 2201/062
USPC ......................... 356/237.5, 237.2; 250/341.1
See application file for complete search history.

(56) References Cited

U.S. PATENT DOCUMENTS

| | | |
|---|---|---|
| 5,870,223 A | 2/1999 | Tomimatsu |
| 8,885,040 B2 | 11/2014 | Puah |
| 2005/0179997 A1 | 8/2005 | Komatsu |
| 2009/0136120 A1 | 5/2009 | Onushkin et al. |
| 2009/0262340 A1 | 10/2009 | Moribe |
| 2011/0285988 A1* | 11/2011 | Menachem ........ G01N 21/8806 356/237.5 |
| 2012/0249779 A1 | 10/2012 | Ji |

FOREIGN PATENT DOCUMENTS

WO    WO2004/077123    9/2004

* cited by examiner

*Primary Examiner* — Sunghee Y Gray
(74) *Attorney, Agent, or Firm* — Defillo & Associates, Inc; Evelyn A Defillo

(57) ABSTRACT

The present invention relates to a device for clearly observing through a microscope, the wafers internal connections of the capsules of the light emitting diodes (LED's), avoiding the dispersion of the light that generates in the transparent dome of the diode capsule and without the need to immerse them in alcohol or any other flammable or hazardous substance classified as dangerous, or to connect the LED's to electrical systems.

5 Claims, 2 Drawing Sheets

DEVICE FOR EXAMINING WAFERS AND WAFER CONNECTIONS IN THE BASE OF THE HOUSINGS OF LIGHT-EMITTING DIODES THROUGH THE TRANSPARENT DOMES THEREOF

CROSS REFERENCE TO RELATED APPLICATION

This application is a national stage entry of PCT/MX2016/000030 filed Mar. 22, 2016, under the International Convention claiming priority over Mexican Patent Application No. MX/a/2015/004603 filed Apr. 10, 2015.

OBJECT OF THE INVENTION

The present invention relates to a device that allows to clearly observe through a microscope the internal connections of the wafers of the capsules of light-emitting diodes (LEDs), preventing the dispersion of the light generated in the transparent dome of the diode capsule without the need to immerse them in alcohol or any other flammable substance or classified as dangerous nor to connect the LEDs to electrical systems.

BACKGROUND

Manufacturers of light emitting diodes must perform visual inspections for the control and quality assurance of internal wiring connections in the diode capsules. In order to carry out the inspection, the manufacturers immerse the diodes in isopropyl alcohol, and with the help of microscopes, they observe through the transparent dome of the diodes wafers and their connections that are located at the bottom of the diodes capsules.

In view of the need to reduce production costs and eliminate the use of alcohol and hazardous substances, the device described below of the present invention was developed and can be used as a tool in the quality assurance and control of the production of light emitting diodes, avoiding the handling of flammable materials.

When the diodes are observed in dry format, the transparent dome of the diode capsule disperses the light and it is not possible to observe the wafer and its connections inside the diode. Submerging the diodes in alcohol, allows the observation, but involves an increase in costs, increase in production times, and the need to adapt the spaces in the production lines for the extraction of vapors, and handling of flammable or hazardous materials.

There are records in patent documents on this subject, such as U.S. Pat. No. 8,885,040, which has an observation device totally different from the device of the present invention; U.S. Patent Application 2009/0136120A1, which discloses an LED inspection device utilizing ultraviolet light; U.S. Patent Application 2012/0249779A1, which discloses a device utilizing both visible and ultraviolet light; as well as the patent application PCT WO2007140984A1, which shows an arrangement of lenses for illumination and observation of the objects. All these documents are totally different from what is proposed by the present invention. The parts and detailed characteristics of this device are clearly shown in the following description and in the accompanying drawings.

DETAILED DESCRIPTION OF THE INVENTION

Figure 1:
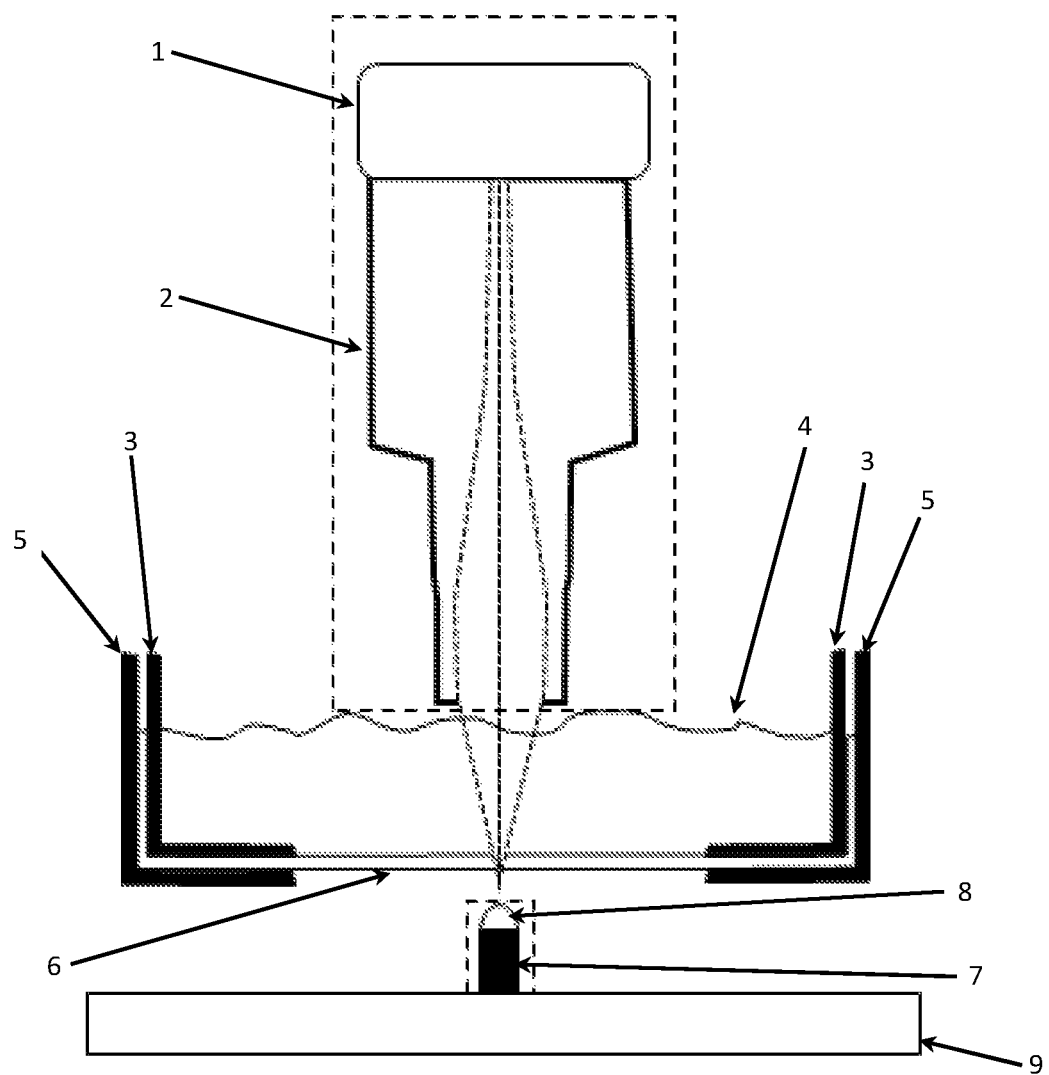
FIG. 1 is a schematic drawing of the device of the present invention before being placed on the light emitting diode. The dotted-line rectangles (----) enclose the portions of the figure, microscope and diode, which are not part of the invention.

The wafer viewing device and its connections at the bottom of the capsule of the light-emitting diode (LED) (7), to which the present invention relates, enables to observe the wafers and their connections inside the light emitting diode (7) through its transparent dome (8) without the need to immerse the diodes in alcohol or some other liquid as has been previously done, or connects the LEDs to electrical systems.

This device includes a container formed by two hollow concentric cylinders (3, 5) which are one inside the other. The cylinders are entirely open at their upper ends while their lower ends have caps which form an integral part of each one of them and which have a circular perforation in the center, which is from a quarter to three quarters of the diameter of the cylinders (3, 5). Between the hollow concentric cylinders (3, 5) is located a transparent and flexible membrane (6) producing an airtight seal.

The transparent and flexible membrane (6) covers the cap of the inner cylinder (3) by way of a hood, covering a portion of the side face thereof, and then, this assembly is introduced to the bottom of the outer cylinder (5). This transparent and flexible membrane (6) can be changed by a new one when the one in use is damaged.

The vessel formed by the two cylinders (3, 5) and the membrane (6) contains water. The water column (4) must reach a height of between three and five centimeters measured from the inner face of the cap of the inner cylinder (5) of the container.

Figure 2:
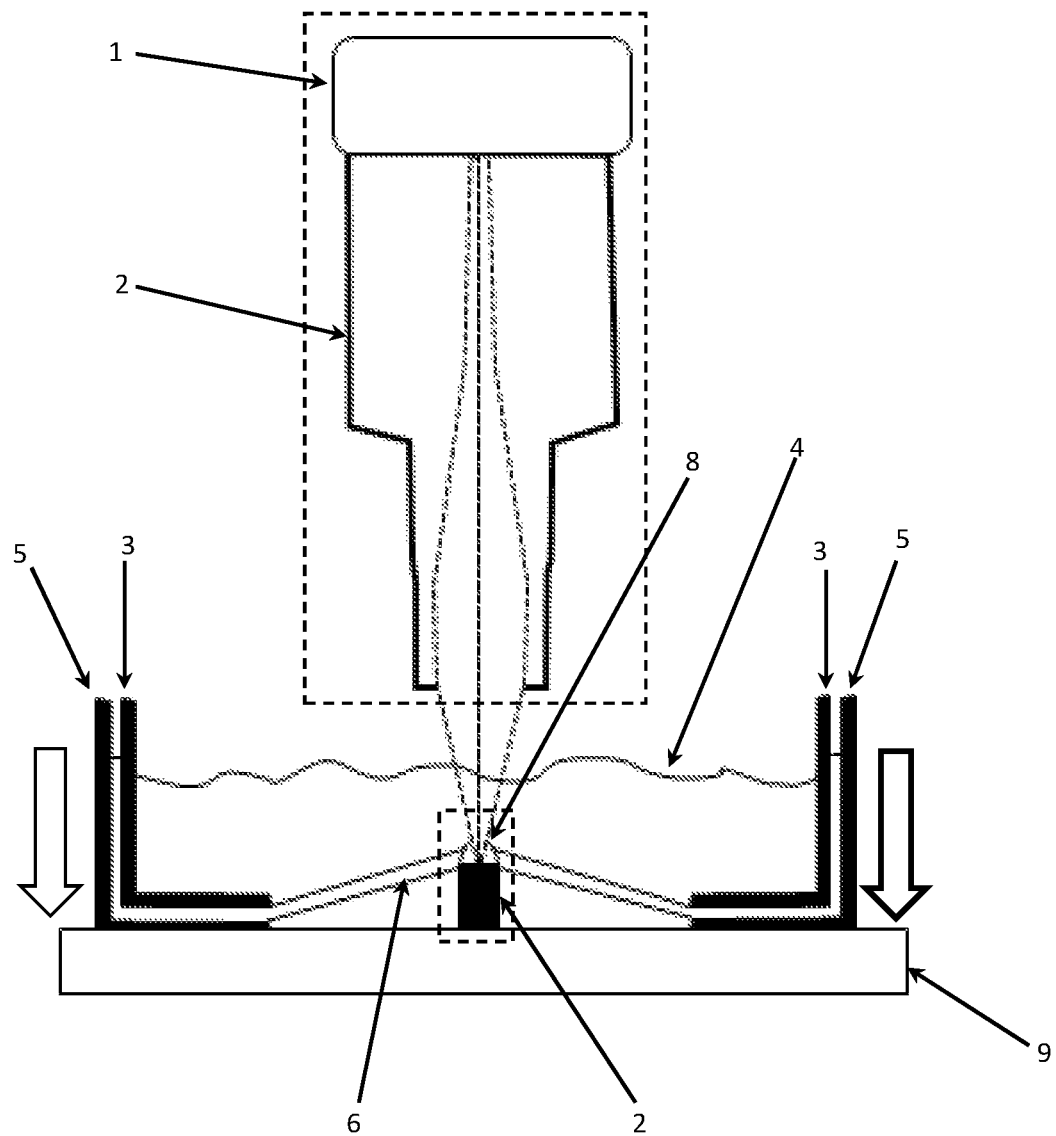
FIG. 2 is a schematic drawing of the device of the present invention positioned and pressed down, as indicated by the side arrows (⇓), on the light emitting diode and ready to be used. It can be seen that the transparent and flexible membrane (6) is placed in close contact with the transparent dome (8) of the light emitting diode (7). The dotted-line rectangles (----) enclose the portions of the figure, microscope and diode, which are not part of the invention.

The vessel with the transparent and flexible membrane (6) and the water (4) is placed on the diode to be observed and pressed downwards, as indicated by the side arrows (⇓) of FIG. 2, on the transparent dome (8) of the capsule of the light emitting diode (7), which is supported by a diode securing rack (9) allowing that the transparent and flexible membrane (6) to tense and take the shape of the transparent dome (8) of the capsule of the light emitting diode (7) forming an impermeable barrier between the transparent dome of the capsule of the diode and the water and preventing the transparent dome from dispersing the light, allowing a clear view of the wafer and its connections inside the diode.

With the vessel placed over the diode, a rapid close-up microscope (2) (zoom by its English acronyms) is positioned, which has a coaxial or angular incident-reflected illumination lamp (1). The present invention works optimally whether the illumination is coaxial or whether the LEDs are oblique just above the diode and at the focal length corresponding to the magnification required to carry out the observation of the wafer connections located at the bottom of the diode capsule.

The water column (4) and the transparent and flexible membrane (6) prevent light from being dispersed, as is the case when immersing the diodes in isopropyl alcohol, but without the problems of flammability and the emission of hazardous vapors.

The device of the present invention enables simultaneous observation of up to 16 light emitting diodes in a single field of view of up to 20.37 millimeters in diameter without the need to immerse them in alcohol or any other flammable or hazardous substance or to connect the LEDs to electrical systems.

The invention claimed is:

1. A device for observing wafers and connections at a bottom of a light emitting diode capsules through transparent domes, the device comprising:
    an outer hollow cylinder having an open top end, sidewalls, a closed bottom end, and a first diameter; an inner hollow cylinder, the inner hollow cylinder is placed concentrically inside the outer hollow cylinder, the inner hollow cylinder having an open top end, sidewalls, a closed bottom end, and a second diameter
    a circular centered perforation located on each one of the closed bottom ends of the outer cylinder and the inner cylinder, each circular centered perforation covering between one-quarter to three-quarters of the diameter of the respective cylinders;
    a transparent and flexible membrane located between the outer hollow cylinder and the inner hollow cylinder.

2. The device according to claim 1, wherein the transparent and flexible membrane covers the closed end of the inner cylinder and a portion of the sidewalls of the outer hollow cylinder.

3. The device according to claim 1, wherein the transparent and flexible membrane is changeable.

4. The device according to claim 1, wherein the device is adapted to contain water.

5. The device according to claim 4, wherein the water inside the device has a height of between three and five centimeters measured from the closed end of the inner hollow cylinder.

* * * * *